United States Patent [19]

Maier

[11] Patent Number: 5,492,873
[45] Date of Patent: *Feb. 20, 1996

[54] PROCESSOR FOR PRODUCING POISON-RESISTANT CATALYSTS

[75] Inventor: Wilhelm F. Maier, Mülheim an der Ruhr, Germany

[73] Assignee: Studiengesellschaft Kohle mbH, Mulheim an der Ruhr, Germany

[*] Notice: The term of this patent shall not extend beyond the expiration date of Pat. No. 5,250,184.

[21] Appl. No.: 191,836

[22] Filed: Feb. 4, 1994

[30] Foreign Application Priority Data

Feb. 9, 1993 [DE] Germany ............... 43 03 610.4

[51] Int. Cl.⁶ .................... B01J 20/28; B01J 23/40
[52] U.S. Cl. .................... 502/4; 502/322; 502/324; 502/325; 502/333; 502/334; 502/354
[58] Field of Search ............... 502/439, 4, 238, 502/239, 304, 332, 333, 334, 354, 322, 324, 325

[56] References Cited

U.S. PATENT DOCUMENTS

| 4,921,823 | 5/1990 | Furneaux et al. | 502/439 |
| 5,030,351 | 7/1991 | Burggraaf et al. | 210/510.1 |
| 5,250,184 | 10/1993 | Maier | 210/510.1 |
| 5,268,101 | 12/1993 | Anderson | 501/12 |

*Primary Examiner*—Anthony McFarlane
*Attorney, Agent, or Firm*—Sprung, Horn, Kramer & Woods

[57] ABSTRACT

The invention relates to a poison-resistant catalytically active microporous membrane to be used for heterogeneously catalyzed reactions, which membrane is characterized in that it is permeable to one of the reactants separated by said membrane, and that it is impermeable to the other reactants and the contaminants contained therein, the molecules of all of which are larger in size than the pore size of the membrane, and to a process for carrying out a heterogeneously catalyzed reaction under conditions preventing the catalyst from being poisoned. This membrane allows to conduct three-phase reactions in a new manner, whereby the reaction gas is directly transported to the active sites.

7 Claims, 14 Drawing Sheets

FIGURE 1: Membrane reactor for separating liquid mixtures.
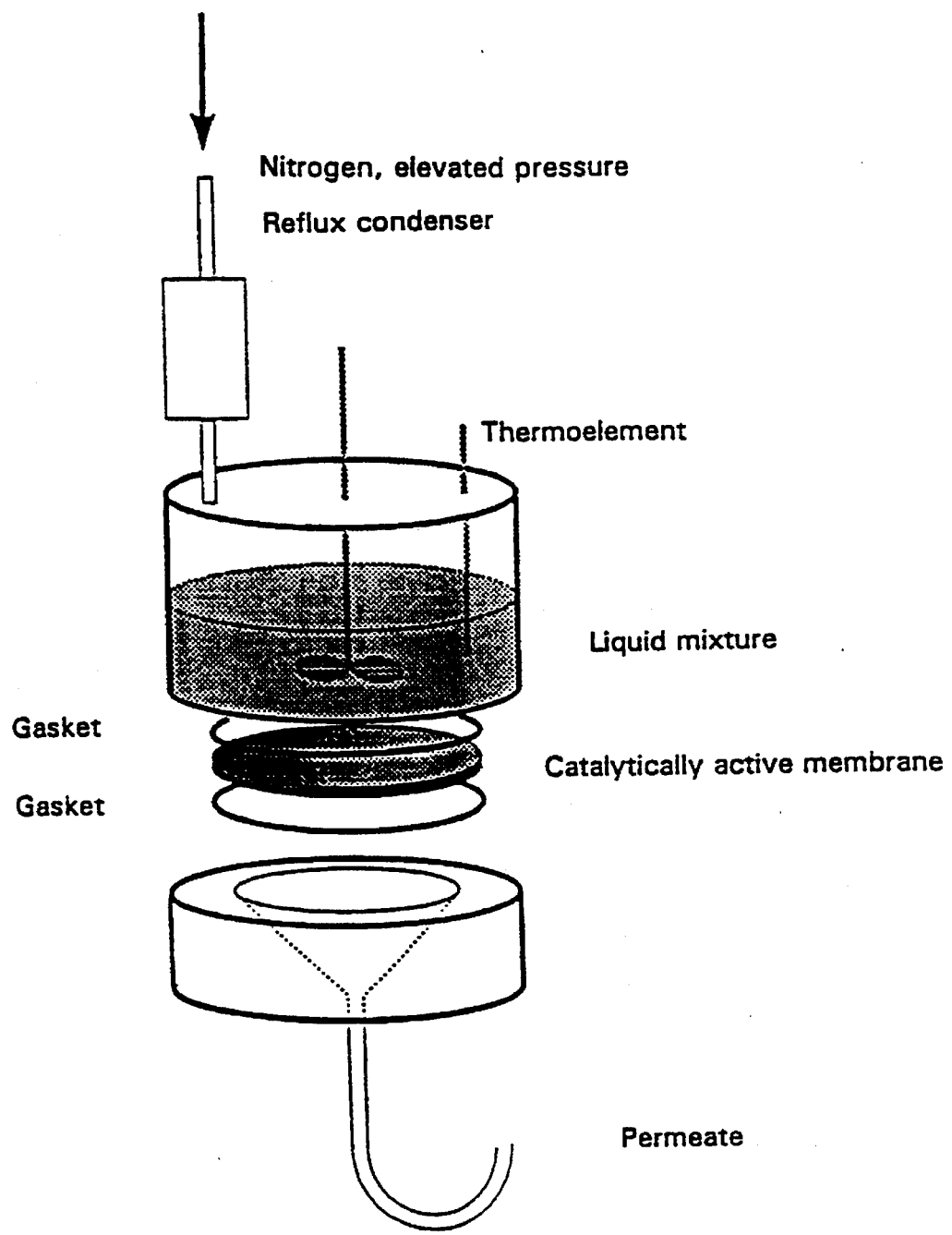

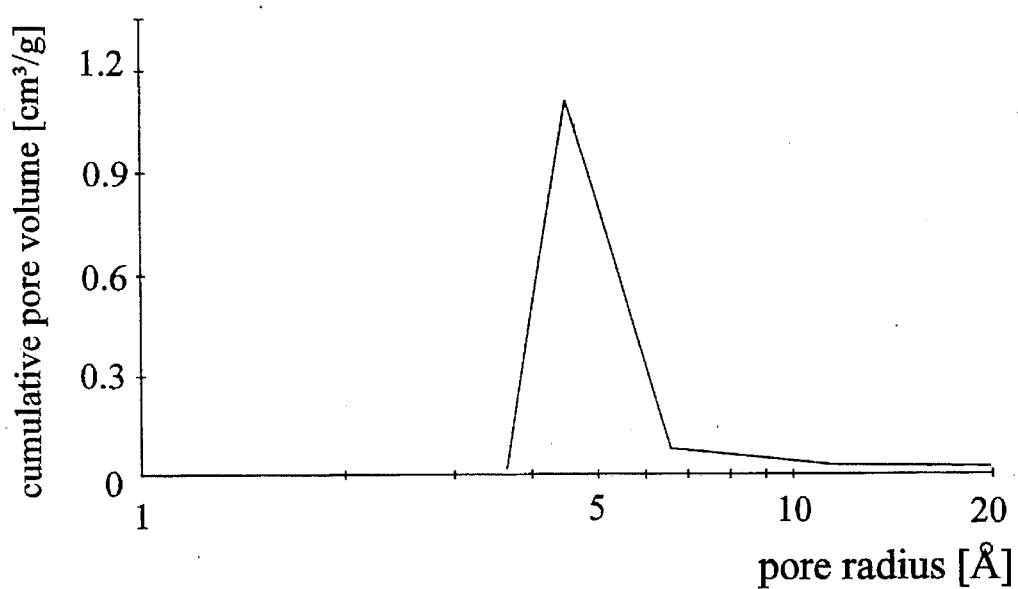
FIGURE 2: Micropore distribution in titanium oxide ceramic, prepared by the sol-gel method. The pore distribution was determined from the $N_2$ isotherm by evaluation according to the method of Horvath and Kawazoe and does not show any mesopores and macropores.

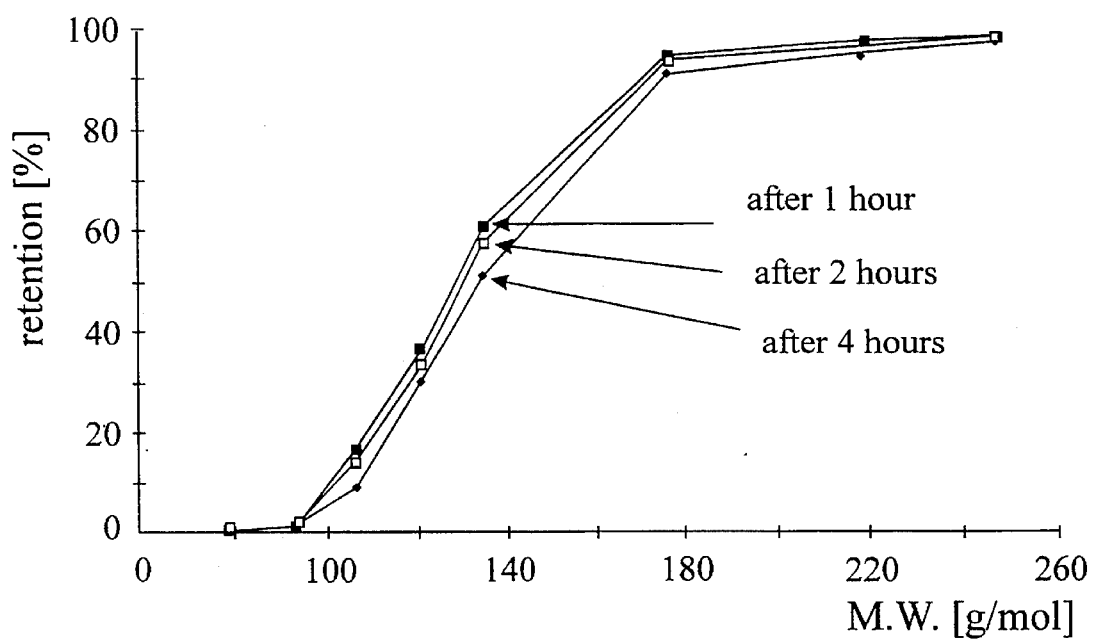
FIGURE 3: Retention of alkyl benzenes on the titanium oxide membrane, relative to benzene, as dependent on the molecular weight.

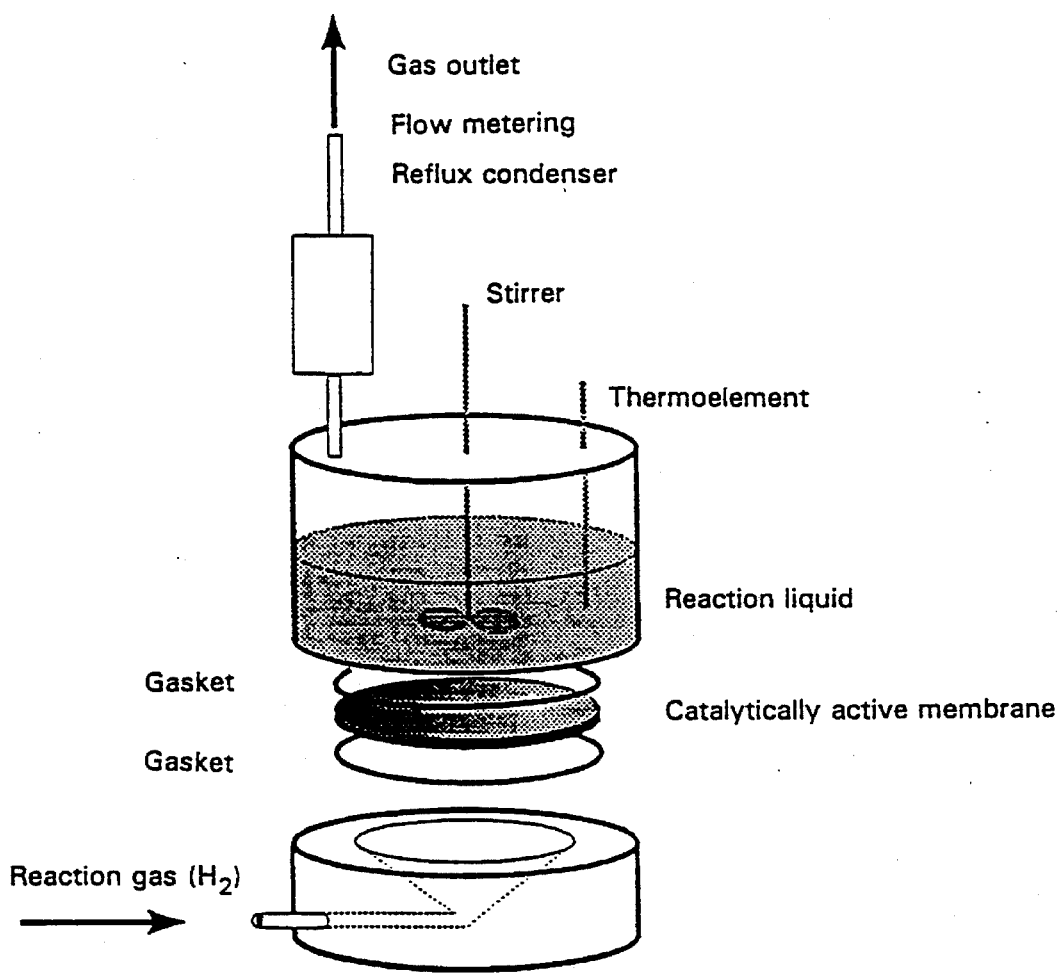
FIGURE 4: Membrane reactor for carrying out multiphase reactions.

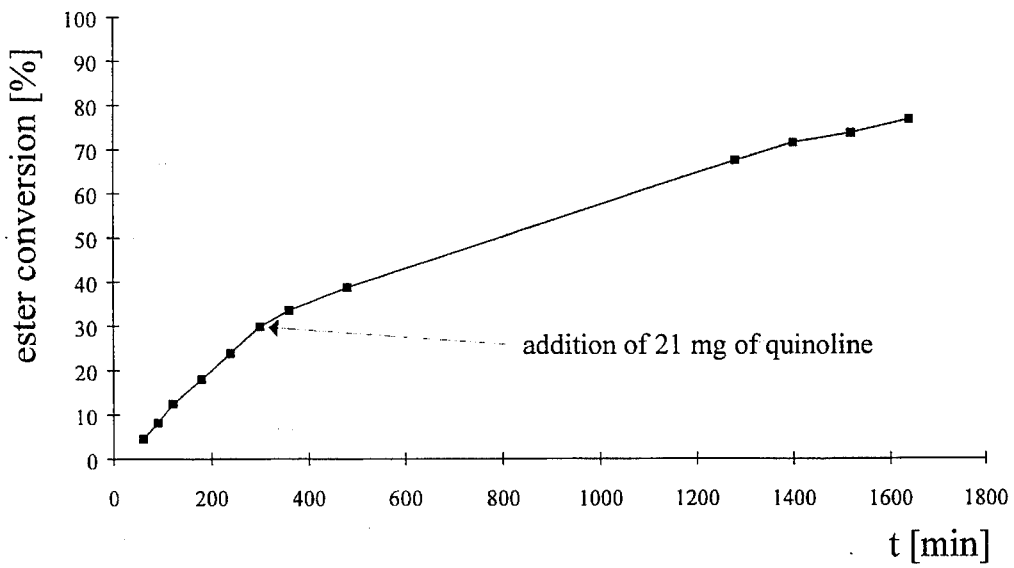
FIGURE 5: Influence of quinoline addition on the hydrogenation of linoleic acid methyl ester in a membrane reactor
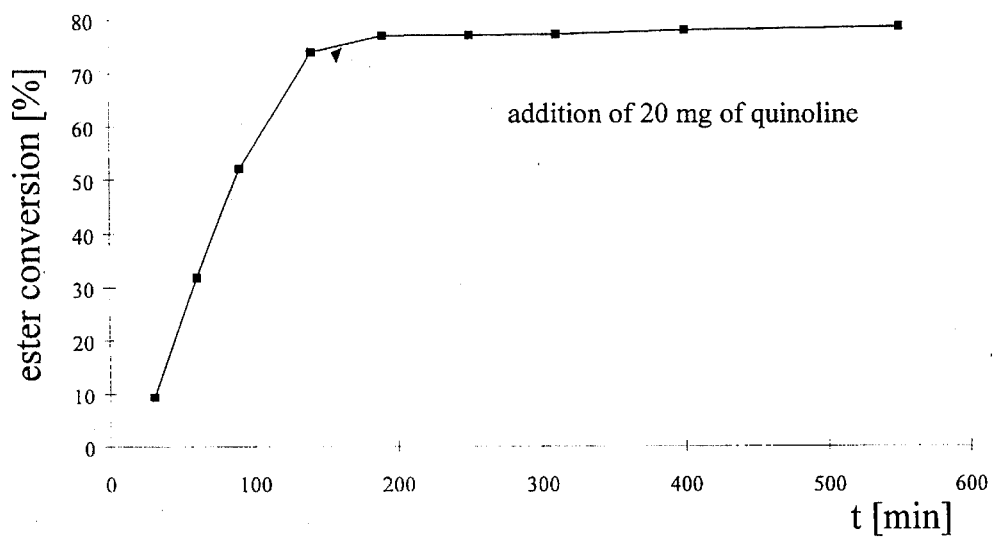
FIGURE 6: Influence of quinoline addition on the hydrogenation of linoleic acid methyl ester in a batch reactor

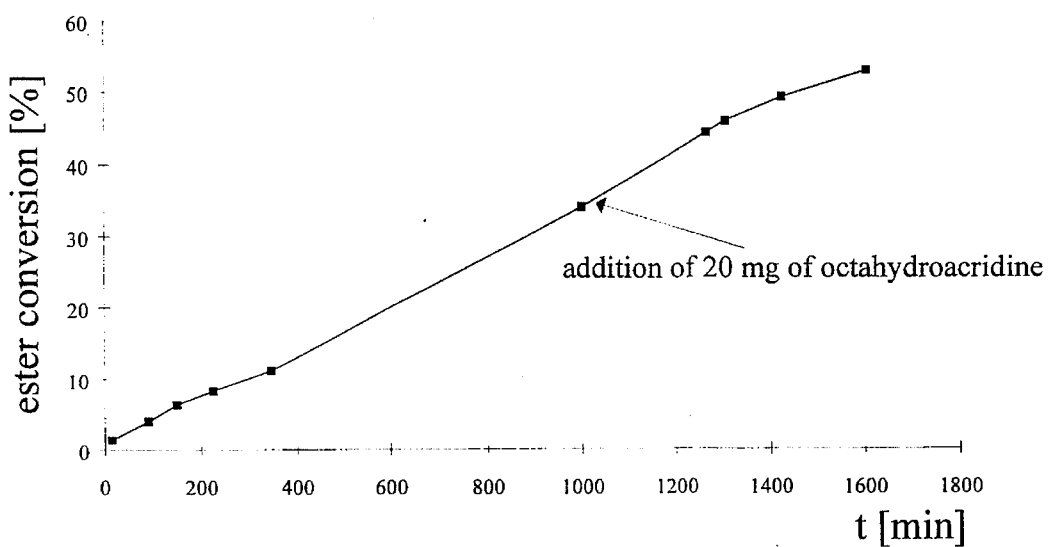
FIGURE 7: Influence of octahydroacridine on the hydrogenation of linoleic acid methyl ester in a membrane reactor
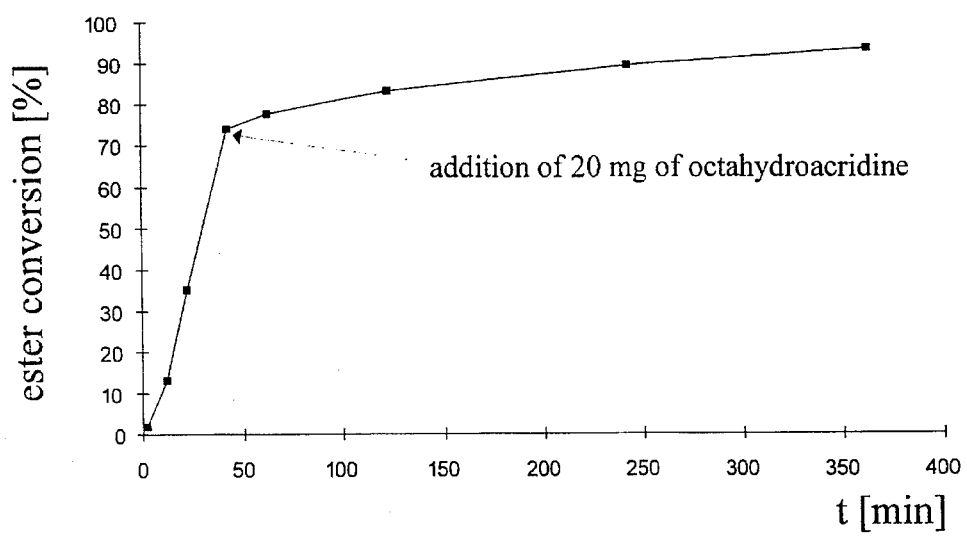
FIGURE 8: Influence of octahydroacridine on the hydrogenation of linoleic acid methyl ester in a batch reactor.

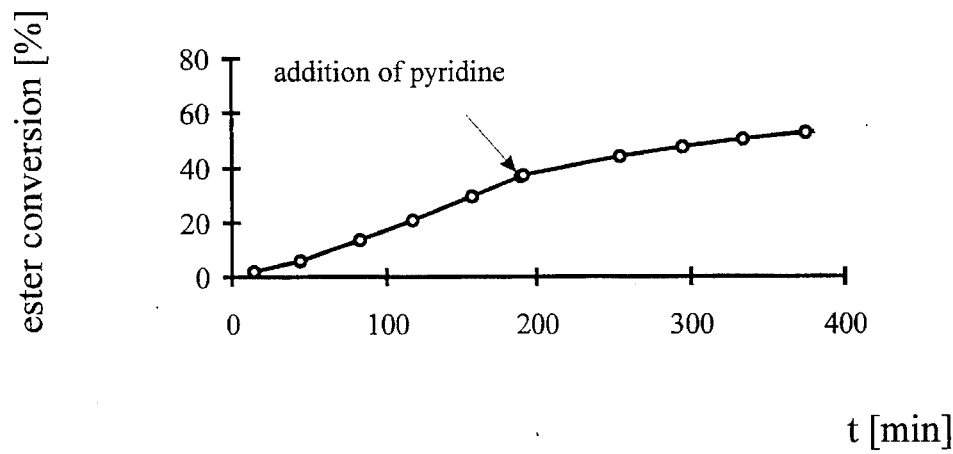
FIGURE 9: Progress of the conversion in the hydrogenation of UDE in a
membrane reactor using a Pt/ZrO$_2$ membran; the arrow
the point of the addition of pyridine
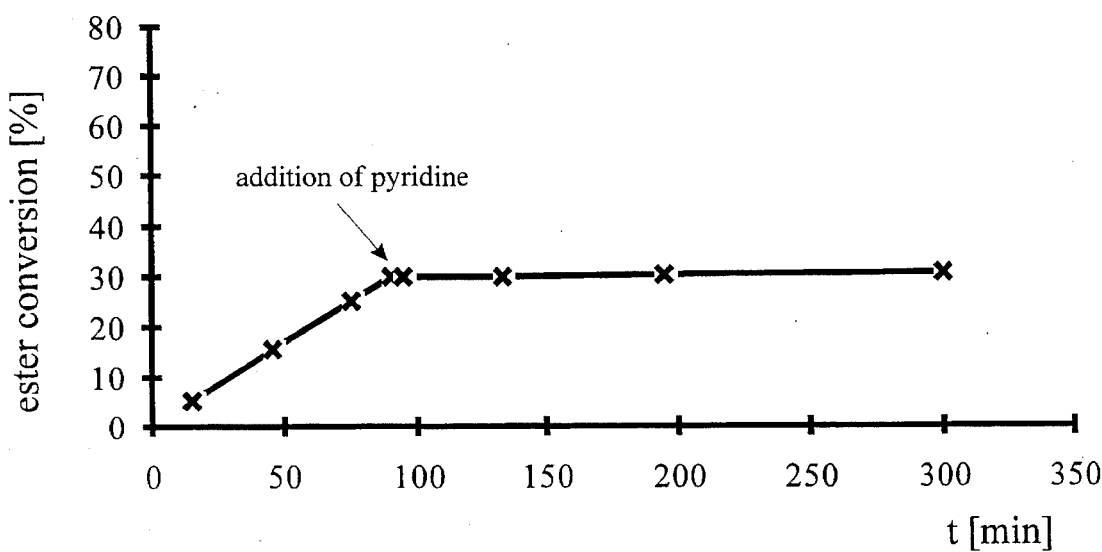
FIGURE 9A: Progress of the conversion in the hydrogenation of UDE in a batch
reactor using the Pt/ZrO$_2$ catalyst; the arrow designates the point
of the addition of pyridine.

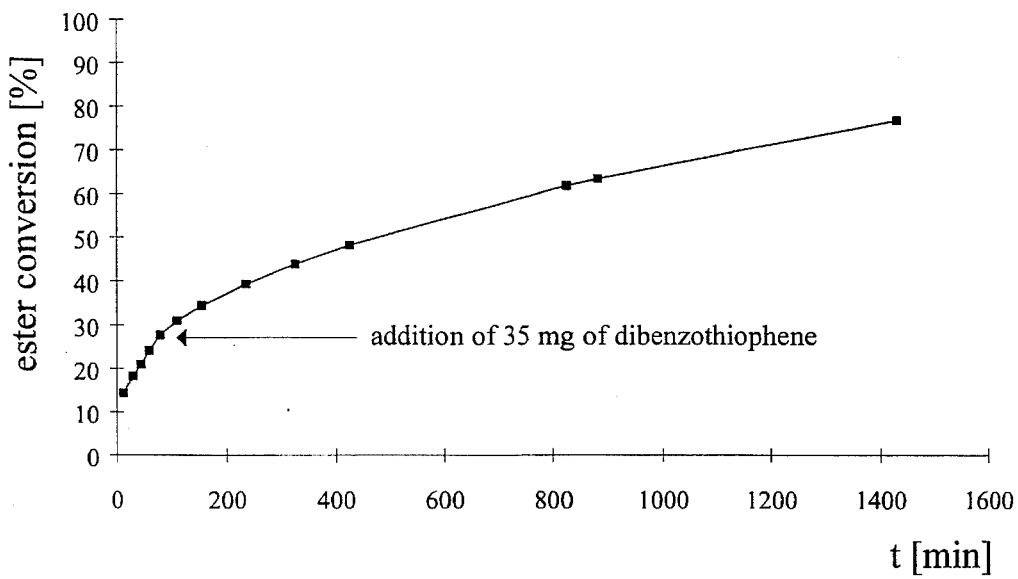
FIGURE 10: Progress of the conversion in the hydrogenation of UDE in the membrane reactor using a Pt/ZrO$_2$ membrane; the arrow designates the point of addition of dibenzothiophene.
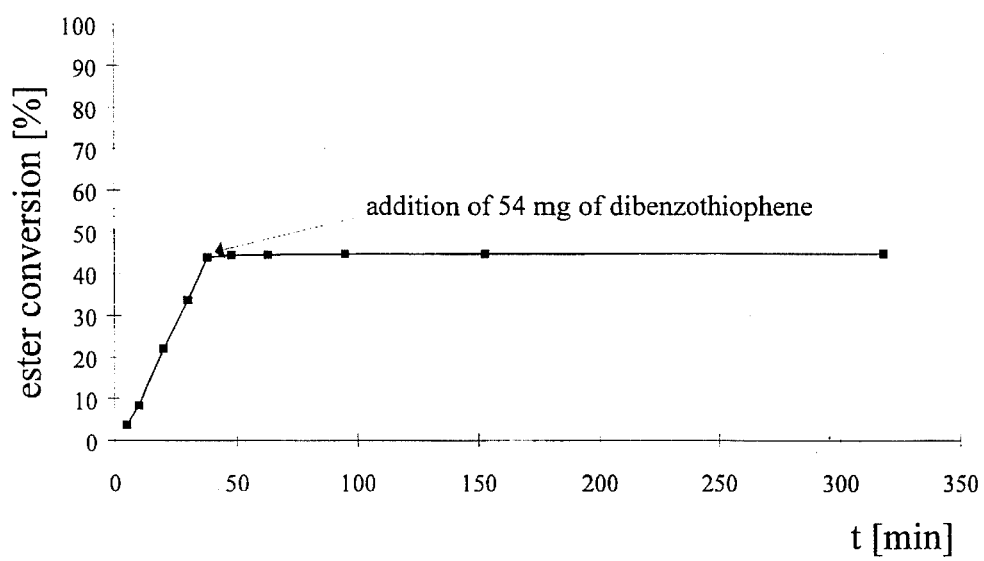
FIGURE 10A: Progress of the conversion in the hydrogenation of UDE in a batch reactor using the Pt/ZrO$_2$ catalyst; the arrow designates the point of the addition of benzothiophene

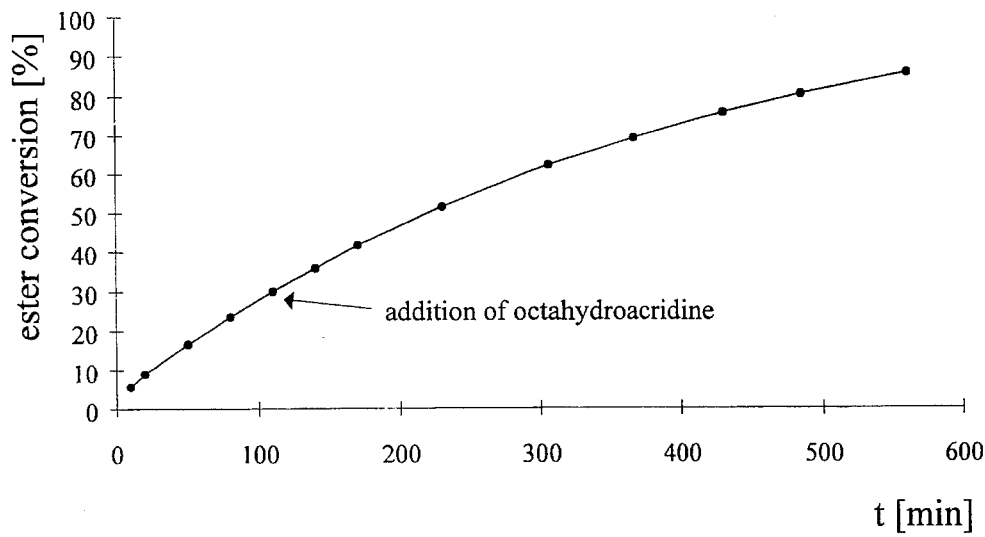

FIGURE 11: Progress of the conversion in the hydrogenation of UDE in a membrane reactor using a Pt/ZrO$_2$ membrane; the arrow designates the point of the addition of octahydroacridine.

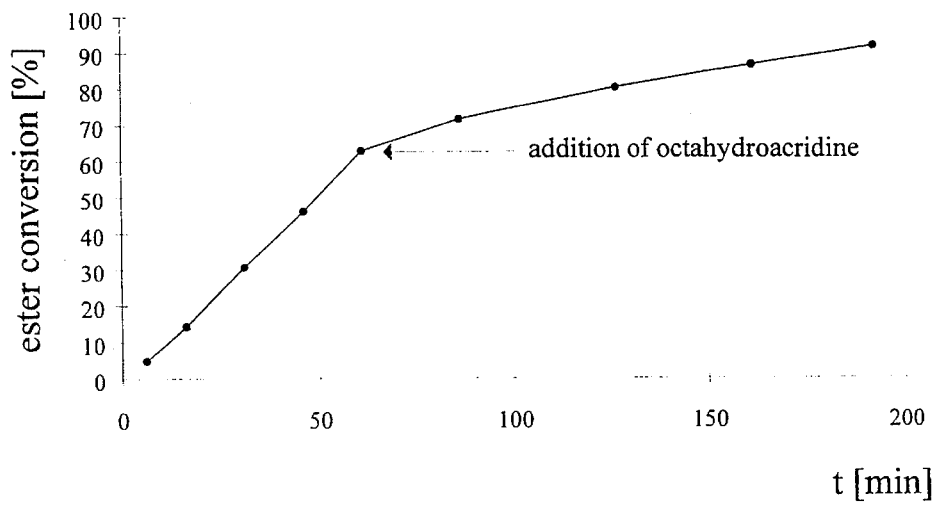

FIGURE 11A: Progress of the conversion in the hydrogenation of UDE in a batch reactor using the Pt/ZrO$_2$ catalyst; the arrow designates the point of the addition of octahydroacridine.

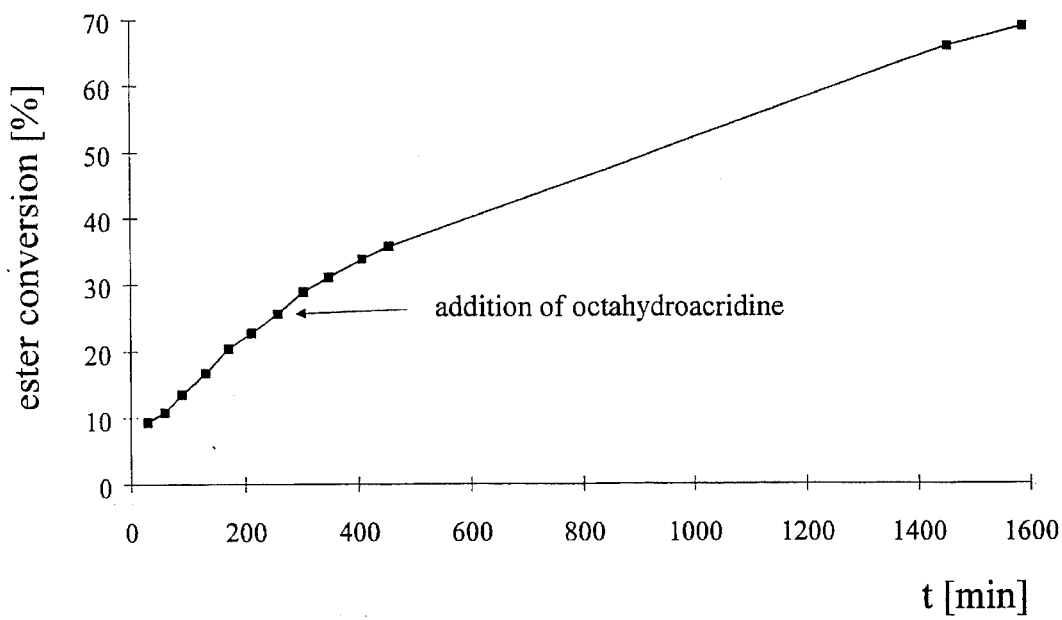

FIGURE 12: Progress of the conversion in the hydrogenation of UDE in a membrane reactor using a Pt/SiO$_2$ membrane; the arrow designates the point of the addition of octahydroacridine.

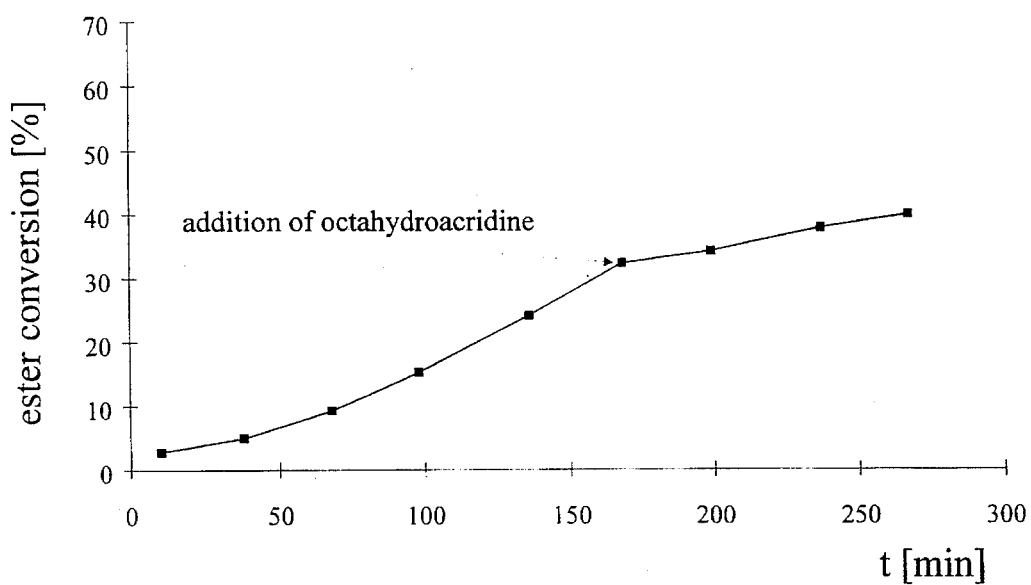

FIGURE 12A: Progress of the conversion in the hydrogeantion of UDE in a batch reactor using the Pt/SiO$_2$ catalyst; the arrow designates the point of the addition of octahydroacridine.

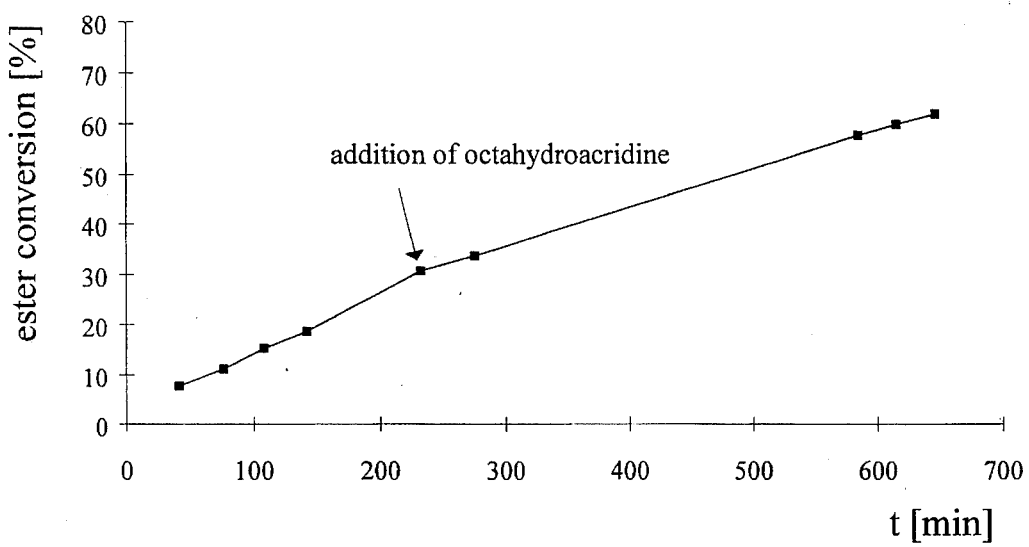
FIGURE 13: Progress of the conversion in the hydrogeantion of UDE in a membrane reactor using a Pt/TiO$_2$ membrane; the arrow designates the point of the addition of octahydroacridine
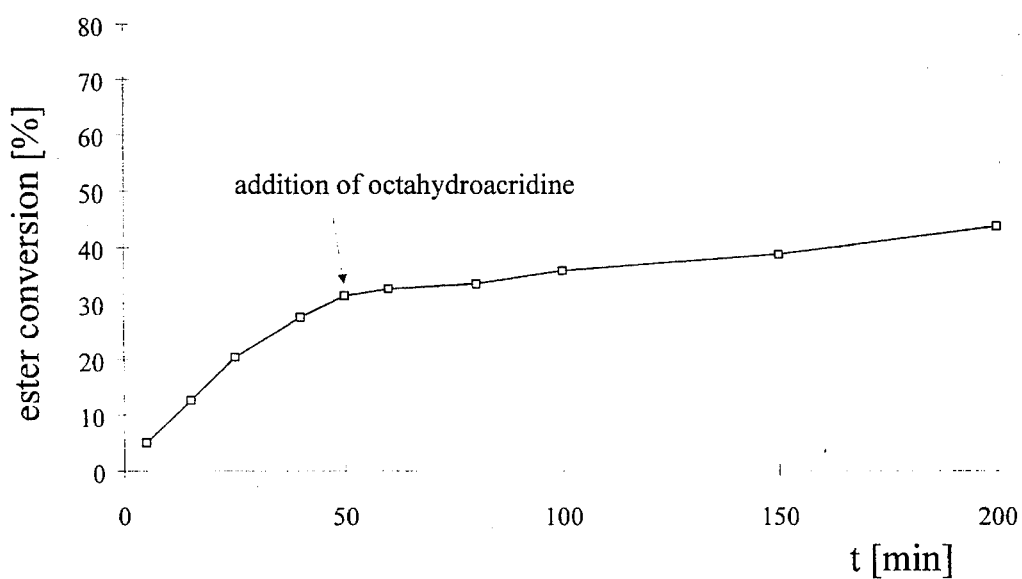
FIGURE 13A: Progress of the conversion in the hydrogenation of UDE in a batch reactor using the Pt/TiO$_2$ catalyst; the arrow designates the point of the addition ooctahydroacridine.

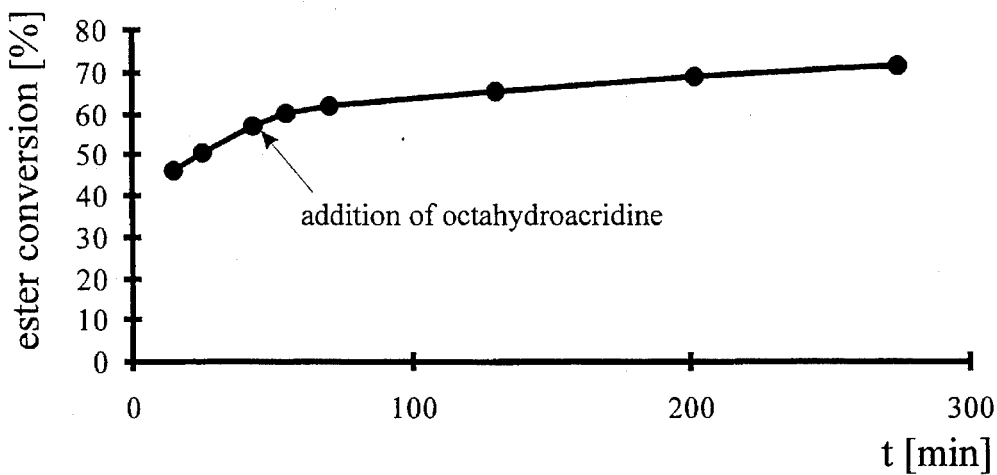
FIGURE 14: Progress of the conversion in the hydrogenation of UDE in a membrane reactor using a $Pt/Al_2O_3$ membrane; the arrow designates the point of octahydroacridine.
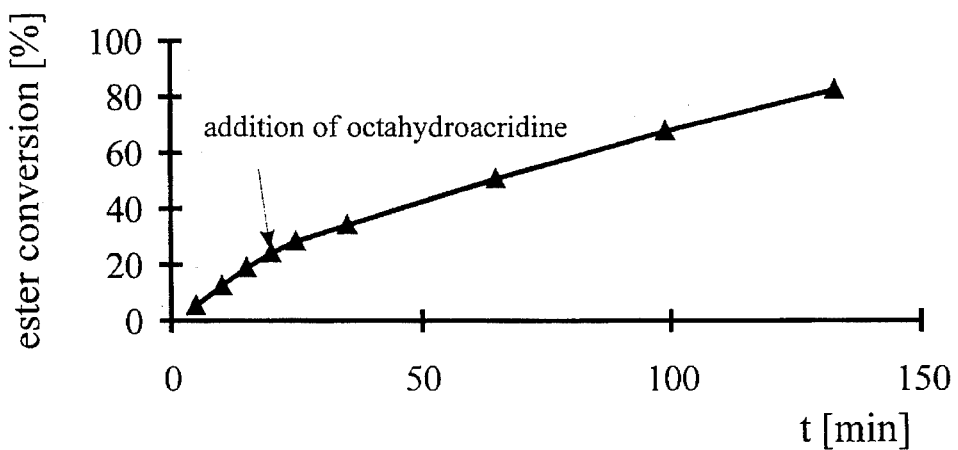
FIGURE 14A: Progress of the conversion in the hydrogenation of UDE in the batch reactor using the $Pt/Al_2O_3$ catalyst; the arrow designates point of addition of octahydroacridine.

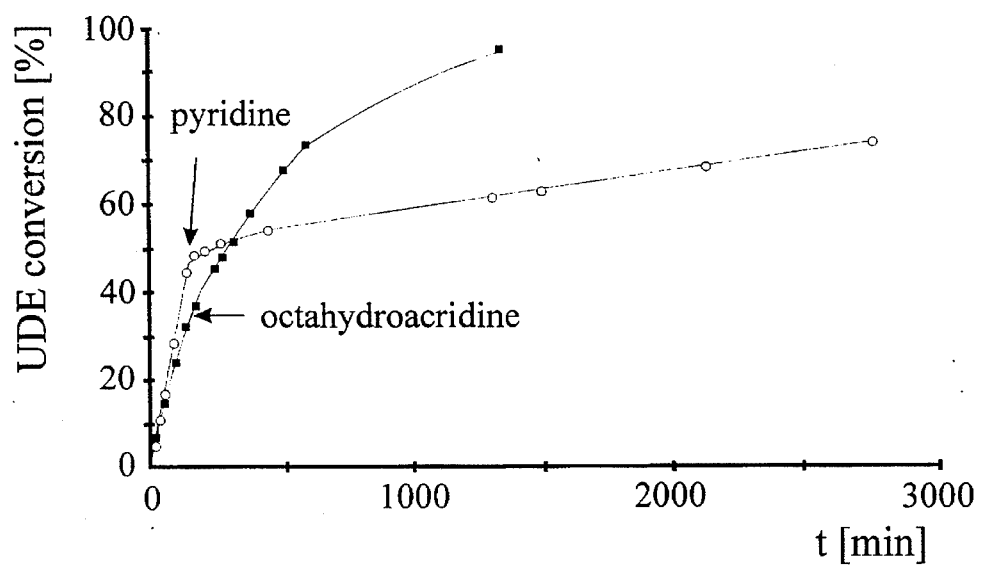
FIGURE 15: Comparison of the progress of the conversion in the hydrogenation of UDE in a membrane reactor using a Pt/ZrO$_2$ membrane upon the addition of the various poisoning substances pyridine and octahydroacridine of different molecular sizes; the arrows designate the points of the addition of the poisoning substances.

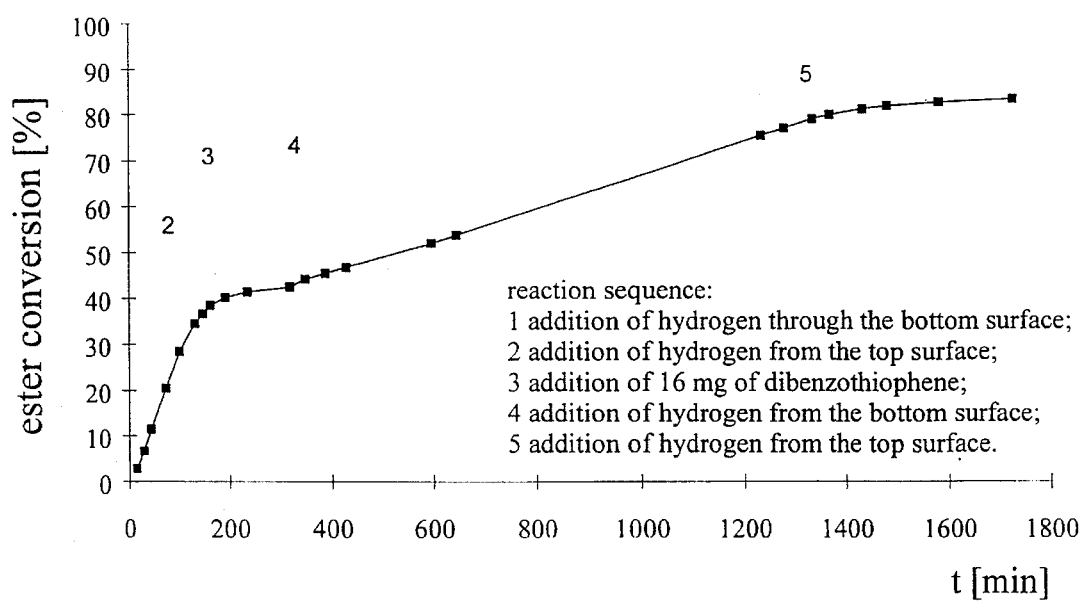
FIGURE 16: Progress of the ester conversion in the hydrogenation of UDE in the membrane reactor using a Pt/ZrO$_2$ membrane upon changes in the conditions of the hydrogen supply through the membrane (from the bottom) and on the surface in contact with the UDE (from the top).

PROCESSOR FOR PRODUCING POISON-RESISTANT CATALYSTS

A major part of the entirety of chemical manufacturing processes is based on heterogeneously catalyzed multiphase reactions, where the catalyst is present in the solid state and the reactants, mostly in the liquid or gaseous state, are passed over the catalyst. In such a process the catalyst will be deactivated (poisoned) in the course of time. Such deactivation or poisoning is mostly caused by undefined contaminants in the liquid phase, which contaminants are deposited on the active sites of the catalyst. Said contaminants often have a molecular weight that is higher than that of the actual molecules of the liquid, are often present only in minimum concentrations, while with the lapse of time they become accumulated on the surface of the catalyst thereby reducing the number of the accessible catalytically active sites.

The use of catalytically active membranes for improving catalytic processes has already been investigated for some time. Thus, palladium is suitable as a membrane for the selective transportation of hydrogen, which property can be utilized for hydrogenation and dehydrogenation reactions {N. Itoh, R. Govind, Membrane Reactor Technology, AIChE Symposium Series 268 (1989) 85; V. M. Gryaznov, V. P. Polyaskova, E. Mikhailovich, E. V. Krapova, U.S. Pat. No. 4,026,958 (1977)}. The high membrane costs and the relatively low permeation rate are supposed to be responsible for that this simple reaction principle hitherto could not find any significant practical application. Ceramic membranes that are distinguished from organic membranes by their increased mechanical strength and temperature resistance as well as chemical resistance are potential materials for applications in the field of gas separation and heterogeneous catalysis. Thus, it could be shown that, in the catalytic dehydrogenation of methanol and butane upon the use of aluminum oxide membranes in the presence of Pt catalysts and ZnO, hydrogen is selectively removed from the reaction zone, so that the conversion and selectivity were improved by a factor of 1.5 over membrane-free reaction conditions {V. T. Zaspalis, W. van Praag, K. Keizer, J. G. van Ommen, J. R. H. Ross, A. J. Burggraaf, Appl. Catal. 74 (1991) 223 and 235}. One important problem inherent to the presently available inorganic materials for membrane reactors is constituted by the pore distribution thereof which, amounting to from 4 nm (40 Å) to 5 µm, is much too large for molecular sieving and an effective gas separation {S. Ilias, R. Govind, JAIChE Symposium Series 268 (1989) 18; H. P. Hsieh, ibid., 53}. Permselective membranes for doubling the selectivity for $C_6$ hydrocarbons by oxidation of propylene with oxygen-selective bismuth membranes were developed by Standard Oil {R. Di Cosimo, J. D. Burrington, R. K. Grasselli, U.S. Pat. No. 4,571,443 (1986)}. The dehydrogenation of hydrogen sulfide can be improved by removing the hydrogen through a membrane {F. Abe, European Patent Application 228 885 (1987)}.

It was now found that catalytically active microporous membranes to be used for heterogeneously catalyzed reactions are poison-resistant, if the membrane is permeable only to one of the reactants separated by said membrane, whereas it is impermeable to the other one of the reactants having a larger molecular size and to contaminants. This membrane allows to conduct three-phase reactions in a new manner, whereby the reaction gas is directly transported to the active sites. Membranes could be successfully prepared, wherein more than 90% of the pores have a pore diameter of less than 1.2 nm. The membranes preferably comprise more than 60% by weight of $SiO_2$, $TiO_2$, $ZrO_2$, $Al_2O_3$ or mixtures thereof. The catalytically active components preferably are Pt, Pd, Ni, Rh, Ir, Ru, Co, Fe, Mn, V, Mo, Bi, Ce, La in an oxidized or reduced catalytically active form or known precursors thereof and are contained in the membranes in an amount of less than 10% by weight. The membranes are prepared by a sol-gel process and are activated in a common manner.

The membrane properties conform to those of the membranes described in DE-OS 41 17 284. The gaseous and liquid reactants are no longer passed over the catalyst as a mixture, but the smaller reactant or reactant gas is supplied by metered addition through the membrane from one surface thereof, while the liquid is present on the opposite surface of the membrane. For this application it is essential that the membrane is a molecular sieve membrane and that the molecules of the liquid are too large for being able to pass through the narrow pores of the membrane. Thereby it is avoided that the contaminants present in the liquid can penetrate to the active sites in the membrane. The reaction gas will get into contact with the catalytically active sites and is activated at these already when travelling through the micropores of the membrane, so that it will react upon exiting from the pores. Thereby, hindrance to the active site, caused by the liquid, of the diffusion is prevented, as it will occur, once the two components are simultaneously fed in the conventional three-phase reactions. In this modified reaction principle as described above, the chemical nature of the reactants is insignificant, since the change presented here in how to conduct the reaction only relies on that there are two reactants present which are different in their sizes, of which the smaller reactant is capable of passing through the catalyst membrane and is also activated during this transportation process, whereas the larger reactant and the contaminants present therewith are not capable of penetrating the pores. For the described modification of how the reaction is conducted it is irrelevant, whether the reaction to be carried out is an oxidation, reduction, addition, substitution or cycloaddition or any other reaction, as long as the reaction partners and reaction poisons can be differentiated by means of the size of the membrane pores.

The absence of a hindrance of the diffusion of the reaction gas may result in milder reaction conditions and an increased activity and selectivity. If the larger reaction component contains contaminants which normally would cause the catalyst to be poisoned, then such poisoning can be prevented, if said contaminants due to their size are not capable of penetrating the pores. Thereby the life time of the catalyst can be increased. In the field of three-phase reactions (gaseous, liquid, solid), this requires a continuous defect-free membrane having a narrow pore size distribution and a maximum pore diameter of less than 1.2 nm, since only a membrane meeting these requirements will be capable of effectively differentiating between gas and liquid molecules. Such membranes have already been described by us in DE-OS 41 17 284. It was shown that by using such membranes comprising additional catalytically active sites the catalysts can be prevented from being poisoned by supplying the reaction gas via a metered addition through the microporous membrane instead of passing it over the catalyst together with the liquid.

What is claimed is a process for carrying out a heterogeneously catalyzed reaction under conditions preventing the catalyst from being poisoned, said process being characterized in that the catalyst is a microporous membrane as specified in claims 1 to 3 and the smaller reactant is supplied by metered addition through the membrane, while the reac- tion liquid (larger reactant) and the contaminants contained therein cannot penetrate the membrane pores due to their molecular sizes.

According to the invention, continuous defect-free catalytically active membranes are prepared by coating a suitable substrate material, using the dip-coating method, with a defect-free thin film of a suitable pre-polymerized inorganic material (sol-gel solution) and drying and firing under controlled conditions. The sol-gel solution needed therefor is produced from the metal alcoholates in the presence of reducible salts of the catalytically active metals according to the sol-gel method with acidic catalysts. Membranes thus prepared are suitable as catalyst membranes only, if they quantitatively retain the larger reactant and only allow the smaller, mostly gaseous, reactant to permeate. Thus, it is recommended to determine the separating property of the catalyst membrane prior to its use as catalyst. We found that molecules having a molecular weight of >180 are almost completely retained by the membranes presented here.

Suitable substrate materials for these membranes are mesoporous or macroporous support membranes comprising symmetric or asymmetric pores having pore diameters larger than 4 nm, but smaller than 2 μm. Such support membranes are commercially available as frits or inorganic membranes from pertinent suppliers. Suitable are only flat, capillary-shaped or tubular support membranes, on which the membrane is prepared as described herein below by dipping into and drawing under controlled conditions from the respective sol-gel solution (dip-coating) and subsequent drying and firing. The membranes thus coated are incorporated in suitable reactors and may be used as catalysts in multiphase reactions at reaction temperatures of up to 500 °C. and under optional reaction pressures. With respect to the reactor design it should be noted that the reactor must be heatable and that the two reactants will have to be supplied on the opposite surfaces of the membrane. Means will have to be provided to allow the membrane to be sealed gas-tight. The apparatus must stand the reaction conditions of the chemical reaction to be carried out. The amount supplied of the smaller reactant must be adjustable via a pressure drop through the membrane towards the larger reactant. Under these conditions, commercially available filtration units and membrane filtering units conforming to the state of the art are usable.

The main ingredients (>50%) of the membranes and of the support membranes are metal oxides of high thermal strength and chemical resistance such as silicon oxides, aluminum oxides, titanium oxides and zirconium oxides and the mixture thereof with optional additives to improve the stability and structure thereof.

We found that catalytically active membranes having a very narrow pore size distribution and a maximum pore size of less than 1.2 nm can be prepared by the sol-gel process. Herein the catalytically active component is a suitable salt, which is well soluble in the initial sol solution, of the catalytically active metal, like those conventionally employed in the manufacture of heterogeneous catalysts. In contrast to the conventionally employed manufacture of the heterogeneous catalyst, our membrane catalyst contains the catalytically active metal as an integral part of its material and not only on its surface. The pore size restriction given applies to the membrane in its catalytically active form. It is essential for the poison resistance performance of the membranes that the membranes are continuous glass-like materials, with the pores being integral parts of the glass. These catalyst membranes are suitable for all heterogeneously catalyzed reactions, wherein the two reactants exhibit significant differences in their sizes.

Such catalytically active membranes may be prepared also by electron beam evaporation as described in DE-OS 41 17 284; to this end, a catalyst metal or catalyst metal oxide in the required amount is added to the metal oxide to be evaporated, followed by simultaneous evaporation thereof.

In addition to the poison resistance of the membrane catalysts, it was found that the catalytic activity of the membranes, when compared to the powdered reference catalyst made of the membrane material, was much higher than could be expected by the low geometric area available for the heterogeneous catalysis (the geometric outer surface area of the finely ground catalyst particles is about 100 times larger than the geometric surface of the membrane). This increase in catalytic activity/outer surface area is attributed to the modified reaction principle, where the smaller reagent diffuses unhindered by the larger reactant to the active site through the microporous, while in the batch reaction the active site is always covered by the molecules of the liquid and thus the diffusion of the smaller reactant to the active site is hindered.

BRIEF DESCRIPTIONS OF THE DRAWINGS

FIG. 1 is a description of a membrane reactor for separating liquid mixtures.

FIG. 2 is a description of a micropore distribution in a titanium oxide ceramic.

FIG. 3 is a description of the retention of alkyl benzene on titanium dioxide membrane.

FIG. 4 is a description of a membrane reactor for carrying out multiphase reactions.

FIG. 5 is a description of the influence of quinoline on the hydrogenation of linoleic acid methyl ester in a membrane reactor.

FIG. 6 is a description of the influence of quinoline on the hydrogenation of linoleic acid methyl ester in a batch reactor.

FIG. 7 is a description of the influence of octahydroacridine on the hydrogenation of linoleic acid methyl ester in a membrane reactor.

FIG. 8 is a description of the influence of octahydroacridine on the hydrogenation of linoleic acid methyl ester in a batch reactor.

FIG. 9 is a description of the progress of the conversion in the hydrogenation of UDE in a membrane reactor.

FIG. 9A is a description of the progress of the conversion in the hydrogenation of UDE in a batch reactor.

FIG. 10 is a description of the progress of the conversion in the hydrogenation of UDE in a membrane reactor with the addition of dibenzothiophene.

FIG. 10A is a description of the progress of the conversion in the hydrogenation of UDE in a batch reactor with the addition of dibenzothiophene.

FIG. 11 is a description of the progress of the conversion in the hydrogenation of UDE in a membrane reactor with the addition of octahydroacridine.

FIG. 11A is a description of the progress of the conversion in the hydrogenation of UDE in a batch reactor with the addition of octahydroacridine.

FIG. 12 is a description of the progress of the conversion in the hydrogenation of UDE in a membrane reactor using Pt/SiO$_2$ membrane with the addition of octahydroacridine.

FIG. 12A is a description of the progress of the conversion in the hydrogenation of UDE in a batch reactor using Pt/SiO$_2$ membrane with the addition of octahydroacridine.

FIG. 13 is a description of the progress of the conversion in the hydrogenation of UDE in a membrane reactor using Pt/TiO$_2$ membrane with the addition of octahydroacridine.

FIG. 13A is a description of the progress of the conversion in the hydrogenation of UDE in a batch reactor using Pt/TiO$_2$ membrane with the addition of octahydroacridine.

FIG. 14 is a description of the progress of the conversion in the hydrogenation of UDE in a membrane reactor using Pt/Al$_2$O$_3$ membrane with the addition of octahydroacridine.

FIG. 14A is a description of the progress of the conversion in the hydrogenation of UDE in a batch reactor using Pt/Al$_2$O$_3$ membrane with the addition of octahydroacridine.

FIG. 15 is a description of the comparison of the progress of the conversion in the hydrogenation of UDE in a membrane reactor using Pt/ZrO$_2$ membrane upon the addition of various poisoning substances.

FIG. 16 is a description of the progress of the conversion in the hydrogenation of UDE in a membrane reactor using Pt/ZrO$_2$ membrane upon changes in the conditions of the hydrogen supply through the membrane.

The invention is further illustrated by the following non-limiting examples.

Pretreatment of the substrate material

A disc of P80 (Königliche Porzellanmanufaktur, Berlin) having a diameter of 47 mm and a thickness of 3 mm was polished on one surface thereof with an abrasive material (grain size 1 μm) and cleaned by boiling it in a 1:1 mixture of acetone and isopropanol (3 hours), sonic treatment in an acetone/isopropanol bath for half an hour and another 3 hours of boiling in acetone/isopropanol. Then the disc was calcined in a muffle furnace at 450° C. for 10 minutes. Then the P80 disk was covered on one surface thereof with a self-adhesive clear sheet (d-c-fix).

The above treatment is necessary only with substrate materials having pore orifices of >30 nm. Substrate materials having pore sizes of <30 nm need only be superficially cleaned.

Preparation of the aluminum sol 9.8 g of a solution of aluminum(III)-2-butylate in 20 ml n-butanol were added to 72 ml of water having a temperature of 90° C. with stirring in a three-neck flask equipped with a reflux condenser. After 2 hours a milky solution had been formed which optically did not further change. Now 8 ml of 0.16N nitric acid were added with a piper, and the solution was boiled to reflux for 2 hours, whereupon the solution became clear and opalescent. Then the solution was further heated while open (in the absence of a reflux condenser), until the alcohol had been evaporated and the temperature of the solution had risen to 100° C. (about 4 hours). Then 20 ml of water were added, and the mixture was further boiled to reflux for 24 hours.

Coating the substrate material with aluminum oxide

Precoating substrate materials having pores of >30 nm

The solution of the aluminum sol {viscosity: 2.320×10$^{-2}$ m$^2$/s (2.320 cSt)} was cooled to room temperature, poured into a polypropylene beaker, and the pretreated P80 disc was submersed in the solution and placed in a desiccator which was then cautiously evacuated until bubble formation had ceased. The beaker containing the solution was placed in a large glass vessel which was covered with a glass plate containing a hole. The P80 disc, which was attached to a string passed through the hole in the glass plate and connected to a drawing motor running vibration-free, was now pulled out from the solution at a drawing rate of 0.5 cm/min as much vibration-free as possible. Pulling was discontinued, once the disc had completely emerged from the solution. The disc, directly hanging over the sol solution was then pre-dried in the closed vessel for one week. Then the disc was heated in air in a dyring oven at 60° C. at a heating rate of 0.2° C./min and maintained at that temperature for 5 hours. Then the disc was heated to 400° C. at a heating rate of 0.1° C./min, maintained at that temperature for 5 hours, and then cooled at a cooling rate of 0.5° C./min. After the disc had been cooled to room temperature, it was directly subjected to a second coating treatment as described above, including the desiccator treatment. The subsequent third coating treatment was carried out without evacuation in the desiccator. Then the large pores of the P80 membrane had been closed to such a degree that they could be coated with the catalytically active membrane.

Preparation of the sol for the manufacture of a Pt-containing catalyst membrane made of titanium dioxide A solution of 11.4 g of titanium(IV)-isopropylate, dissolved in 150 ml of 99% ethanol, was stirred for 30 minutes, followed by dropwise addition of 0.4 ml of a 2N nitric acid at room temperature. After another 30 minutes, 95 mg of sodium hexachloroplatinate, dissolved in 5 ml of ethanol, were added. A clear yellowish solution was obtained. This solution was further stirred at room temperature for 4 hours and then had a viscosity of 1.973×10$^{-2}$ m$^2$/s (1.973 cSt). Coating using this solution was immediately carried out.

Manufacture of the catalytically active membrane

Prior to coating, the atmosphere was enriched with ethanol by vigorously stirring 100 ml of ethanol in a glass beaker for 10 minutes. Then the membrane was pulled out from the prepared Pt-containing catalyst sol in the same manner as described above for coating with aluminum oxide, dried and calcined to a maximum temperature of 300° C.

Examination of the separation performance of the membranes

The dry membrane was heated in a reactor (see FIG. 1) at 250° C. under dry nitrogen at an excess pressure of 1 bar for 5 hours (pore size distribution see FIG. 2). It was then cooled to 70° C., and 8 ml of a solution of equal parts by weight of benzene, toluene, ethylbenzene, propylbenzene, butylbenzene, heptylbenzene, decylbenzene and dodecylbenzene were stirred under nitrogen at an excess pressure of 1 bar on the membrane for 1 hour. Then the compositions of permeate and feed were analyzed by gas chromatography. FIG. 3 shows the relative retention of the various alkylbenzenes.

EXAMPLE 1

Influence of quinoline on the hydrogenation of linoleic acid methyl ester in the membrane reactor In a membrane reactor (see FIG. 4) an excess hydrogen pressure of about 1 to 1.5 bar was applied to the bottom surface of the dry catalyst membrane, so that a flow rate of 6 to 10 ml/min was observed at the gas outlet. The reactor was slowly heated to 250° C., and the membrane was activated at that temperature for 2 hours and then cooled to 100° C. Then 0.1 ml of linoleic acid methyl ester, dissolved in 15 ml of n-dodecane were injected into the reactor and hydrogenated while stirred in a hydrogen stream (flow rate: 30 ml/min). The reaction was monitored every hour by sampling and gas chromatographic analysis which showed the expected linear increase of conversion over time. After 30% of conversion, 21 mg of quinoline were added as a model poison. It was found that the rate of reaction was reduced by 10% upon the addition of the poison while, however, the reaction continued to proceed unchanged (see FIG. 5).

CONTROL EXAMPLE 1

Influence of quinoline on the hydrogenation of linoleic acid methyl ester in the batch reactor As a control experiment, the hydrogenation of linoleic acid methyl ester was carried out under conventional reaction conditions in a batch reactor. The remainder of the Sol from preparing the membrane catalyst was dried, fired and ground in the same manner as the membrane and used as reference catalyst (1% Pt/TiO$_2$; analytical data: BET surface area 269 m$^2$/g, pore diameter 0.8 nm). 0.1 ml of linoleic acid methyl ester in 15 ml of n-dodecane and 13 mg of said catalyst were hydrogenated under hydrogen at atmospheric pressure and 100° C. with vigorous stirring. The reaction was monitored every hour by sampling and analyzed by gas chromatography. After a conversion of 70%, 20 mg of quinoline were added as a model poison, which resulted in an immediate and complete termination of the reaction (see FIG. 6). This experiment demonstrates that the same catalyst material which, when used as catalyst membrane, is hardly susceptible to being poisoned, is poisoned upon use as catalyst powder in a batch reactor in the same manner as conventional catalysts are.

The suppression of poisoning is related to the pore size of the membrane and the size of the poisoning molecules. This is why the suppression of the poisoning effect is observed to an even higher degree for larger poisoning molecules. This is demonstrated by using octahydroacridine as the poisoning molecule.

EXAMPLE 2

Influence of octahydroacridine on the hydrogenation of linoleic acid methyl ester in the membrane reactor The experiment was carried out in the same manner as the preceding membrane catalysis experiment. 20 mg of the model poison octahydroacridine were added after a conversion of 35%. A decrease in the rate of the hydrogenation after this addition was hardly noticeable, which fact shows that octahydroacridine, due its molecular size, penetrates the pores even less and, thus, exhibits an even lower poisoning action than quinoline does (see FIG. 7).

CONTROL EXAMPLE 2

Influence of octahydroacridine on the hydrogenation of linoleic acid methyl ester in the batch reactor The experiment was carried out in the same manner as the preceding hydrogenation experiment in the batch reactor. 0.1 ml of linoleic acid methyl ester in 15 ml dodecane were hydrogenated with 5 mg of catalyst at 100° C. at atmospheric pressure with a stirring speed of 500 rpm. After a conversion of 75%, 21 mg of octahydroacridine were added, whereupon the hydrogenation rate decreased to $\frac{1}{27}$ (see FIG. 8). This demonstrates that octahydroacridine under conventional reaction conditions (without a membrane) almost completely deactivates the catalyst.

Preparation of the sol for the manufacture of a catalyst membrane made of zirconium dioxide In a 250 ml polyvinyl beaker, 13.7 g of zirconium(IV)-butylate were added dropwise with vigorous stirring to 150 ml of 99% ethanol. After 30 minutes, 0.75 ml of water in 45 ml of ethanol were very slowly added dropwise. Some minutes later 150 μl of 4N nitric acid were added dropwise. After a short time the solution became clear, and then a solution of 108 mg of hexachloroplatinate in 10 ml of ethanol was added dropwise. The clear yellow solution was sealed with Parafilm and after 4 hours was ready to be used for coating the support membrane.

Manufacture of the 1% Pt/zirconium dioxide control catalyst

The sol-gel solution remaining after coating was loosely sealed with Parafilm and allowed to sit under a fume hood for 6 days. Then the Parafilm was removed and the gel was dried under a fume hood for another 2 weeks. Now the material was dried in the same manner as described for the manufacture of the membranes. Analytical data: BET surface area 125 m$^2$/g, pore diameter 0.9 nm).

Preparation of the sol for the manufacture of a catalyst membrane made of silicon dioxide In a 250 ml polypropylene beaker, to 110 ml of tetra-ethoxy-silane there were added dropwise with stirring 85 ml of ethanol. 16 ml of 8N hydrochloric acid and a solution of 739 mg of hexachloroplatinum hydroxide in 15 ml of ethanol were added dropwise in sequence at an addition rate of 5 ml/min. The clear yellow solution while further stirred was sealed with Parafilm and after 4 hours was ready to be used for coating the support membrane as described above.

Manufacture of the 1% Pt/silicon dioxide control catalyst

The sol-gel solution remaining after coating was loosely sealed with Parafilm and further stirred for 1 day and then, without stirring, allowed to sit sealed under a fume hood for 6 days. Then the Parafilm was removed and the gel was dried under a fume hood for another 2 weeks. Now the material was dried in the same manner as described for the manufacture of the membranes. Analytical data: BET surface area 651 m$^2$/g, pore diameter 1 nm).

Preparation of the sol for the manufacture of a catalyst membrane made of aluminum oxide In a 100 ml three-neck flask equipped with a reflux condenser, 72 ml of water were heated to 90° C. A solution of 9.8 g of aluminum(III)-isobutylate in 20 ml of isobutanol was poured into the vigorously stirred hot water. The mixture was stirred for 2 hours, and then 1.2 ml of 2N nitric acid and a solution of 118.6 mg of sodium hexachloroplatinate in 10 ml of isopropanol were added dropwise, and the solution was boiled at 86° C. under reflux for 4 hours. Then the alcohols were distilled off, 25 ml of water were added, and the mixture was stirred overnight at 90° C. under a reflux condenser. The solution was cooled to room temperature, transferred into a polyvinyl beaker and sealed with Parafilm. Thus, the solution was ready to be immediately used for coating the support membrane as described above.

Manufacture of the 1% Pt/aluminum oxide control catalyst

The sol-gel solution remaining after coating was loosely sealed with Parafilm and further stirred for 1 day and then, without stirring, allowed to sit sealed under a fume hood for 6 days. Then the Parafilm was removed and the gel was dried under a fume hood for another 2 weeks. Now the material was dried in the same manner as described for the manufacture of the membranes. Analytical data: BET surface area 312 m$^2$/g, pore diameter 1–2 nm).

EXAMPLES 3 to 10

In the following experiments, 10-undecenoic acid ethyl ester (UDE) was employed in the place of linoleic acid ester. All of the catalytic reactions were carried out at 50° C. The catalyst membrane was 47 mm in diameter. In the batch reactor, there were employed in all cases 0.3 ml of UDE in 6 ml of dodecane. In the batch reactor, the amounts of catalyst were always 12 to 13 mg, except for the Pt-aluminum oxide where only 6 mg were used. In the membrane reactor, there were employed in all cases 0.2 ml of UDE in 7 ml of dodecane. The various poisoning substances tested, the amounts thereof employed and the time of poison addition is evident from the description of the experiments and the FIGURES. All examples are commented together with Control Examples.

EXAMPLE 3

FIG. 9 demonstrates the course of the hydrogenation of UDE on the Pt/zirconium dioxide membrane prior to and after the addition of 35 mg of pyridine (minor decrease in the hydrogenation rate). FIG. 9A demonstrates the complete poisoning of the control catalyst in the hydrogenation in the batch reactor upon the addition of 53 mg of pyridine.

EXAMPLE 4

FIG. 10 shows a slight reduction in the rate of hydrogenation of UDE on the Pt/zirconium dioxide membrane upon the addition of 35 mg of dibenzothiophene. FIG. 10A demonstrates the complete poisoning of the control catalyst in the hydrogenation in the batch reactor upon the addition of 53 mg of dibenzothiophene.

EXAMPLE 5

FIG. 11 shows that the hydrogenation of UDE on the Pt/zirconium dioxide membrane is hardly affected by the addition of 35 mg of octahydroacridine. FIG. 11A shows that the hydrogenation of UDE on the control catalyst in the batch reactor is significantly poisoned upon the addition of 53 mg of octahydroacridine.

EXAMPLE 6

FIG. 12 demonstrates that the rate of the hydrogenation of UDE on the Pt/silicon dioxide membrane is not affected by the addition of 35 mg of octahydroacridine. FIG. 12A shows that the rate of the hydrogenation of UDE on the control catalyst in the batch reactor is severely reduced due to poisoning upon the addition of 56 mg of octahydroacridine.

EXAMPLE 7

FIG. 13 shows that the hydrogenation of UDE in the membrane reactor using the Pt/titanium dioxide membrane is hardly poisoned by the addition of 35 mg of octahydroacridine.

FIG. 13a shows that the hydrogenation of UDE in the batch reactor using the Pt/titanium dioxide control catalyst is severely poisoned by the addition of 53 mg of octahydroacridine.

EXAMPLE 8

FIG. 14 demonstrates the degree of poisoning in the hydrogenation of UDE on the Pt/aluminum oxide membrane upon the addition of only 18 mg of octahydroacridine. The membrane employed is distinguished from the above membranes by larger pores (2 nm) so that a prevention of the catalyst poison from penetrating into the catalyst pores is no longer ensured. FIG. 14A shows the degree of poisoning of the control catalyst in the hydrogenation of UDE in the batch reactor upon the addition of 52 mg of octahydroacridine.

This experiment demonstrates, how easily a catalytically active membrane is poisoned, if the pore size thereof is such as to allow a penetration of the poisoning substance into the membrane.

EXAMPLE 9

Experiments for distinguishing membrane poisoning caused by poisoning substances that are different in size FIG. 15 shows a comparison of the courses of the hydrogenations of UDE in a membrane reactor on the Pt/zirconium dioxide membrane under otherwise identical conditions upon the additions of the poisoning substances pyridine (43 mg) and octahydroacridine (43 mg), respectively, which are different in their molecular sizes. As a result of these experiments, the smaller pyridine which is still capable of penetrating the pores of the membrane exhibits an essentially higher poisoning effect than that produced by the comparably large octahydroacridine.

EXAMPLE 10

Experiments for distinguishing the hydrogenations via active sites inside the pores and on the outer surface as accessible to the liquid FIG. 16 shows the course of the hydrogenation of UDE in a membrane reactor on the Pt/zirconium dioxide membrane. In the beginning of the reaction (FIG. 16, Point 1), hydrogen was supplied to the membrane from below (excess pressure of 1.2 bar), while 0.1 ml of UDE in 6 ml of dodecane were stirred on the upper membrane surface. After about 100 minutes, the hydrogen supply from below was turned off, and a pressure-free hydrogen flow of 30 ml/min was passed over the upper membrane surface of the reactor (FIG. 16, Point 2). The hydrogenation rate first remained the same, while after about 30 minutes it distinctly decreased (drop of hydrogen pressure on the lower membrane surface). It is supposed that the reduction in the hydrogenation rate to the largest part thereof is attributable to the Pt sites accessible on the upper surface of the membrane. After 3 hours, the addition of 16 mg of dibenzothiophene (FIG. 16, Point 3) caused the hydrogenation to be almost completely poisoned, which fact indicates an effective poisoning of the freely accessible Pt sites. After 6 hours (FIG. 16, Point 4) the hydrogen supply on the upper membrane surface was turned off, and the excess hydrogen pressure on the lower membrane surface was again adjusted to 1.2 bar. The significant increase in the hydrogenation rate shows that now again the Pt sites inside the membrane are active and control the hydrogenation. The hydrogenation proceeds continuously during 13 hours and reaches a conversion in excess of 80%. At FIG. 16, Point 5, again the hydrogen supply from the lower membrane surface was turned off (slow pressure drop), and again the upper membrane surface was purged with a flow of 30 ml/min of pressure-free hydrogen. Again it is seen that the hydrogenation is almost completely poisoned. This experiment demonstrates that in the use of membrane catalysts the active Pt sites present on the outer surfaces of the membranes are poisoned in the same manner as with conventional catalysts, whereas the active sites present inside the pores of the membranes are accessible only to hydrogen, but not to the substrate or the catalyst poisons and will not be poisoned.

The investigations show that the poison-resistance of membrane catalysts is not restricted to titanium dioxide, but that it can also be realized with other membrane catalysts, more specifically those made of the oxides of silicon, zirconium and aluminum. The kind of poison is independent of the molecular structure and of the kind of the extraneous atoms. It is the molecule size that governs membrane poisoning, as is evident from the decrease in poison-resistance upon the action of pyridine which has a smaller molecule.

EXAMPLE 11

In the same manner as in the hydrogenation experiments described above, 2 g of palm oil in 15 ml of dodecane were hydrogenated with hydrogen in a membrane reactor on the 1% Pt/TiO$_2$ membrane. No poisoning was observed.

EXAMPLE 12

In the same manner as in the hydrogenation experiments described above, 2 g of fish oil in 15 ml of dodecane were hydrogenated with hydrogen in a membrane reactor on the 1% Pt/TiO$_2$ membrane. No poisoning was observed.

EXAMPLE 13

In the same manner as in the hydrogenation experiments described above, 2 g of crack fatty acid in 15 ml of dodecane were hydrogenated with hydrogen in a membrane reactor on the 1% Pt/TiO$_2$ membrane. No poisoning was observed.

EXAMPLE 14

A microporous 1% Pd/ZrO$_2$ membrane was prepared with sodium tetrachloropalladate in the same manner as the above-described preparation of the Pt/ZrO$_2$ membrane. With this palladium-containing membrane, 2 g of palm oil in 15 ml of dodecane were hydrogenated with hydrogen in a membrane reactor. No poisoning was observed.

These experiments demonstrate that technical fats may be hydrogenated in a membrane reactor under poison-resistant conditions using the membranes developed here.

I claim:

1. A poison-resistant continuous membrane for heterogeneously catalyzed reactions permeable to one of the reactants separated by said membrane, the membrane having pores distributed throughout of which more than 90% have a pore diameter smaller than 1,2 nm, the membrane containing as integral part thereof in said pores at least one catalytically active component.

2. The membrane according to claim 1, characterized in that more than 60% by weight of the membranes consist of $SiO_2$, $TiO_2$, $ZrO_2$, $Al_2O_3$ or mixtures thereof.

3. The membrane according to claim 1, characterized in that said membrane has been produced by electron beam evaporation of the metal oxide and the catalytically active metal or metal oxide admixed therewith.

4. The membrane according to claim 1 wherein less than 10% by weight of the membrane consists of catalytically active components.

5. The membrane according to claim 1 wherein the catalytically active components are selected from the group consisting of Pt, Pd, Ni, Rh, Ir, Ru, Co, Fe, Mn, V, Mo, Bi, Ce, and La wherein said components are in an oxidized or reduced catalytically active form.

6. The membrane according to claim 5, characterized in that said membrane has been produced in accordance with a sol-gel process with the addition of a soluble derivative of catalytically active metals and activating said membrane.

7. The membrane according to claim 1 containing at least two catalytically active substances in said pores.

* * * * *

UNITED STATES PATENT AND TRADEMARK OFFICE
CERTIFICATE OF CORRECTION

PATENT NO. : 5,492,873
DATED : February 20, 1996
INVENTOR(S) : Wilhelm F. Maier

It is certified that error appears in the above-indentified patent and that said Letters Patent is hereby corrected as shown below:

| | |
|---|---|
| Title Page & Col 1 line 1 | Invention [54]" Delete "PROCESSOR " and substitute -- PROCESS -- |
| Col. 12, claim 6 line 1 | Delete claim " 5 " and substitute claim -- 1 -- |
| Col. 12, claim 6 line 3 | After " derivative of " insert -- the -- |

Signed and Sealed this

Twentieth Day of August, 1996

Attest:

BRUCE LEHMAN

*Attesting Officer*  *Commissioner of Patents and Trademarks*